United States Patent
Hällgren

(12) 
(10) Patent No.: US 6,576,429 B1
(45) Date of Patent: Jun. 10, 2003

(54) APPARATUS FOR INTESTINAL SAMPLING AND USE THEREOF

(75) Inventor: Roger Hällgren, Bälinge (SE)

(73) Assignee: Alimenta Diagnostics AB, Uppsala (SE)

( * ) Notice: Subject to any disclaimer, the term of this patent is extended or adjusted under 35 U.S.C. 154(b) by 0 days.

(21) Appl. No.: 09/697,573

(22) Filed: Oct. 26, 2000

Related U.S. Application Data

(60) Provisional application No. 60/163,033, filed on Nov. 2, 1999.

(30) Foreign Application Priority Data

Oct. 26, 1999 (SE) .................................................. 9903872

(51) Int. Cl.[7] ...................... G01N 33/53; G01N 33/543; G01N 33/558; A61B 19/00
(52) U.S. Cl. ................ 435/7.1; 435/4; 435/6; 435/7.9; 435/287.1; 435/287.2; 435/287.3; 435/287.7; 435/287.9; 435/288.5; 435/288.7; 435/176; 435/177; 436/174; 436/178; 436/518; 436/524; 436/528; 436/536; 436/807; 436/811; 604/1; 604/11; 604/19; 604/21; 604/27; 604/317; 604/403; 604/915; 128/898
(58) Field of Search ............................. 128/898; 604/1, 604/11, 19, 21, 27, 317, 403, 915; 422/68.1; 435/4, 6, 7.1, 7.9, 287.1, 287.2, 287.3, 287.7, 287.9, 288.5, 288.7, 174–177; 436/174, 178, 518, 524, 528, 536, 807, 811

(56) References Cited

U.S. PATENT DOCUMENTS

| 3,877,464 A | | 4/1975 | Vermes ........................ 128/2 B |
| 4,735,214 A | | 4/1988 | Berman ........................ 128/759 |
| 5,312,343 A | * | 5/1994 | Krog et al. ............. 604/101.03 |
| 5,983,899 A | * | 11/1999 | Hallgren ..................... 128/898 |
| 5,984,860 A | * | 11/1999 | Shan ........................... 600/110 |

FOREIGN PATENT DOCUMENTS

| EP | 0219461 | | 4/1987 |
| WO | WO 90/05304 A1 | * | 5/1990 |
| WO | WO 9532668 | | 12/1995 |

\* cited by examiner

Primary Examiner—Long V. Le
Assistant Examiner—Kartic Padmanabhan
(74) Attorney, Agent, or Firm—Dinsmore & Shohl LLP

(57) ABSTRACT

An apparatus for taking an intestinal sample of a human or animal patient comprises a holder part (1) and an expandable part (2) supported by the holder part and having one or more sampling areas (8) on the surface thereof. The expandable part (2) is in a non-expanded state rectally insertable into and retractable from the patient's intestine, and in an expanded state, inserted into the patient's intestine, the expandable part is capable of contacting the intestinal wall with at least one sampling area (8; 14). The apparatus further comprises protective livers (7a, 7b) for preventing said sampling area or areas (8) from contact with the intestinal wall and intestinal fluid at least when the expandable part (2) in the non-expanded state is being rectally inserted into the patient's intestine.

27 Claims, 4 Drawing Sheets

APPARATUS FOR INTESTINAL SAMPLING AND USE THEREOF

RELATED APPLICATION

The present application claims priority under 35 U.S.C. §119(e) of U.S. provisional application Ser. No. 60/163,033 filed Nov. 2, 1999.

TECHNICAL FIELD OF THE INVENTION

The present invention relates to the study of pathological changes in the gastrointestinal system, and more particularly to an apparatus for taking intestinal samples as well as to the use thereof.

BACKGROUND OF THE INVENTION

Among the various techniques that are used today to study pathological changes in the gastro-intestinal system are X-ray contrast examination, computerized tomography and magnetic resonance tomography. Endoscopy, i.e. insertion into the gastrointestinal tract of a stomach or intestinal viewer (gastroscopy, colonoscopy, rectoscopy) makes it possible to inspect the intestinal wall and to take samples from the intestinal mucous membrane (biopsy) which then may be examined by e.g. microscopy. Recently, also intestinal perfusion systems have been used. All these techniques are expensive, time-consuming and more or less trying to the patient. There is therefore a need for a simple methodology that makes it possible to study pathological processes in the intestinal mucous membrane without using biopsy or perfusion.

WO 95/32668 discloses a rectal instrument to be used in allergy diagnosis and designed for insertion into the colonic tract to take samples from the lumen of the large intestine after provocation of the mucous membrane with an allergen. The instrument comprises a tube-like element having a terminal part that is expandable, specifically an inflatable balloon. Subareas on the balloon have a diffusable allergen absorbed or adsorbed thereto, and on the same or separate subareas, a receptor(s) for one or more inflammation markers, usually antibodies specific to the relevant marker (s), are bound to the balloon. The instrument is inserted into the rectum, whereupon the balloon is inflated such that the outer surface of the balloon contacts the mucous membrane. The allergen diffuses to the rectal mucous membrane and, if the individual concerned is allergic to the allergen in question, will cause the release of inflammation markers which in turn diffuse to the lumen where they eventually are captured by the receptor(s) on the balloon surface. After the marker or markers have been released and bound to the balloon, the balloon is deflated and the device is removed and analyzed with respect to the bound marker(s).

The above instrument has, however, the drawback that the areas with diffusible allergen and the areas with immobilized receptor on the balloon surface may be damaged by contact with the internal sphincter when inserted and retracted through the patient's anus. It may also be mentioned, that, generally, immobilizing receptors on the balloon surface could cause problems in that hazardous residues from the coupling of the receptor(s) may remain on the surface.

SUMMARY OF THE INVENTION

The present invention aims at overcoming the disadvantages of the prior art devices or instruments and provide an apparatus for rectal insertion for studying pathological processes in the intestinal mucous membrane without the use of biopsy or perfusion. Like the instrument described in WO 95/32668 above, the apparatus of the present invention is based on contacting an expandable part thereof with the intestinal wall for sampling, and optionally also for provocation of the intestine with allergen.

According to a basic concept of the invention, however, the sampling area(s) and provocation area(s), when present, of the expandable part essentially are protected from contact with the intestinal wall when the expandable part is inserted and retracted from the colon through the patient's anus.

The present invention therefore provides an apparatus for taking an intestinal sample in a human or animal patient, comprising a holder part and an expandable part supported by the holder part and having at least one sampling area. In a non-expanded state of the expandable part, the expandable part is rectally insertable, and in an expanded state, the sampling area or areas of the expandable part are capable of contacting the intestinal wall. The apparatus is characterized in that it comprises means for protecting the sampling area or areas from contact with the intestinal wall and intestinal fluid when the expandable part in its non-expanded state is rectally inserted into the intestinal tract.

Preferably, the apparatus comprises means for protecting the sampling area or areas also when removing the expandable part from the intestine.

While essentially the whole area of the expandable part could be a sampling area, it is preferred that one or preferably, more subareas thereof are used as sampling areas and provocation areas.

The sampling area or areas on the expandable part may have one or more receptors for, for example, an inflammation or cancer marker or the like bound to the. surface thereof (similarly as in the device described in WO 95/32668 above). Such inflammation markers may, for example, be derived from neutrophilic granulocytes, eosinophilic granulocytes, mast cells/basophilic granulocytes, or may be a cytokine, a prostaglandin or a plasma protein, such as albumin.

While the sampling area or areas in this case may have the receptor(s) immobilized directly to the surface of the expandable part, it is preferred that the sampling area or areas comprise a surface element of suitable material attached to the expandable part surface. Such a material may exhibit a two-dimensional surface to which the receptor or receptors are immobilized, or constitute a three-dimensional matrix structure in which the receptor or receptors are immobilized in depth.

Alternatively, and at least in some aspects also preferably, the sampling area or areas comprise absorbing material (without any immobilized receptor) capable of effectively sucking up water and substances dissolved therein (such as proteins, enzymes, hormones etc) when contacted with the intestinal mucosa, such that the content of such substances in the absorbed material may be analyzed. After sampling, a reactant or reactants may be added directly to the absorbing material to detect the presence of a certain substance or substances through a colour reaction or similar.

Usually, however, the absorbing material is removed from the expandable part after sampling and the absorbed substances extracted and analyzed separately by various analytical methods, such as electrophoresis, radioimmunological techniques, enzyme immunosorbent assay (ELISA) or nephelometry, just to mention a few.

While it is within the scope of the present invention that the apparatus may be designed for sampling at arbitrary sites along the intestinal tract, it is presently preferred to take samples in the lumen of the large intestine. Such sampling may, for example, advantageously be used for testing for markers for allergy, especially food allergy including e.g. celiac disease, after provoking the colonic mucosa with a desired allergen(s), e.g. gluten (as described in the above-mentioned WO 95/32668).

The expandable part is advantageously an inflatable member of a flexible or elastic material, for example a balloon or an elastic tubular member.

In one embodiment of apparatus according to the present invention, the sampling area or areas on the expandable part are protected by a protective cover until the expandable part has reached the desired section of the intestine to be studied. Prior to or after expanding the expandable part, the cover is removed, e.g. mechanically by pulling means provided on or associated with the apparatus part outside the body, to permit sampling by contacting the sampling area or areas with the intestinal wall.

In another embodiment, the sampling area or areas on the expandable part are protected by a cover which may be opened in connection with the sampling and then be re-closed over the sampling area(s) after the sampling is completed. Such a cover may, for example, be of capsule or shell type, for instance a two-part shell or capsule wherein the two parts together, preferably with some overlap, cover the sampling area(s) in the non-expanded state of the expandable part, but which are removed from and expose the sampling area(s) in the expanded state.

In still another embodiment, the expandable part is displaceably mounted (e.g. telescopically) within the holder part of the apparatus so that the expandable part is kept within the holder part during the rectal insertion and retraction of the apparatus, and brought out of the holder part at the test site to be expanded. In yet another embodiment, the sampling area or areas on the expandable part are depressed in relation to the remaining surface of the expandable part when the latter is in its non-expanded state to thereby prevent contact with the intestinal wall. If, for example, the expandable part is a balloon or elastic tube or cylinder with sampling elements on the surface, the holder part supporting the balloon or elastic tube may have a recess or recesses for receiving each sampling element when the balloon is deflated.

Like the apparatus described in WO 95/32668, the expandable part may also comprise means for allergen presentation to provoke the intestine before the sampling.

Such means may be the surface itself of the expandable part or a special element(s) having the allergen(s) diffusively bound or adsorbed thereto. The allergen-presenting area(s) will, of course, also be protected by the protective means at the same time as the sampling area(s). Optionally, the allergen-presenting area or areas may be the same as the sampling areas.

DETAILED DESCRIPTION OF THE INVENTION

Figure 1A:
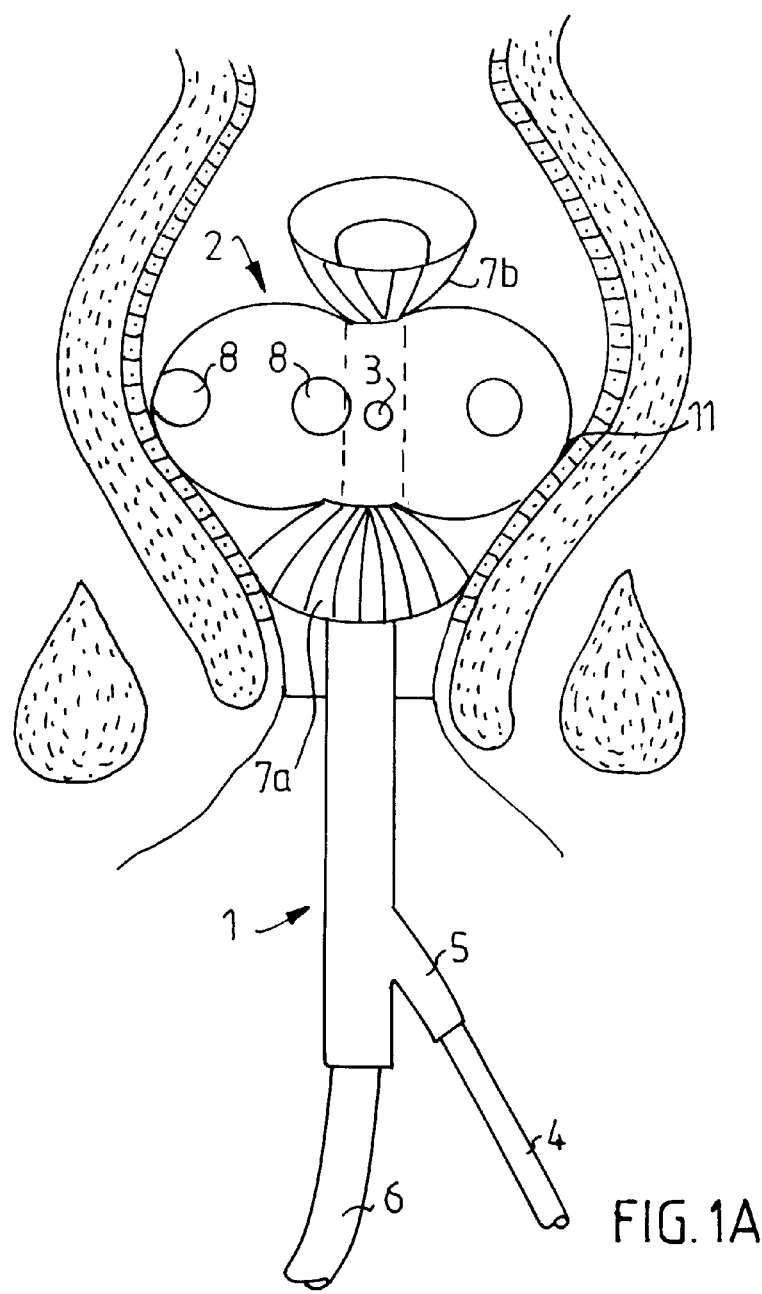
FIG. 1A is a schematic perspective and partly sectional view of an embodiment of an apparatus of the present invention with the expandable part of the apparatus in its expanded state and applied in the rectum of a patient.
Figure 1B:
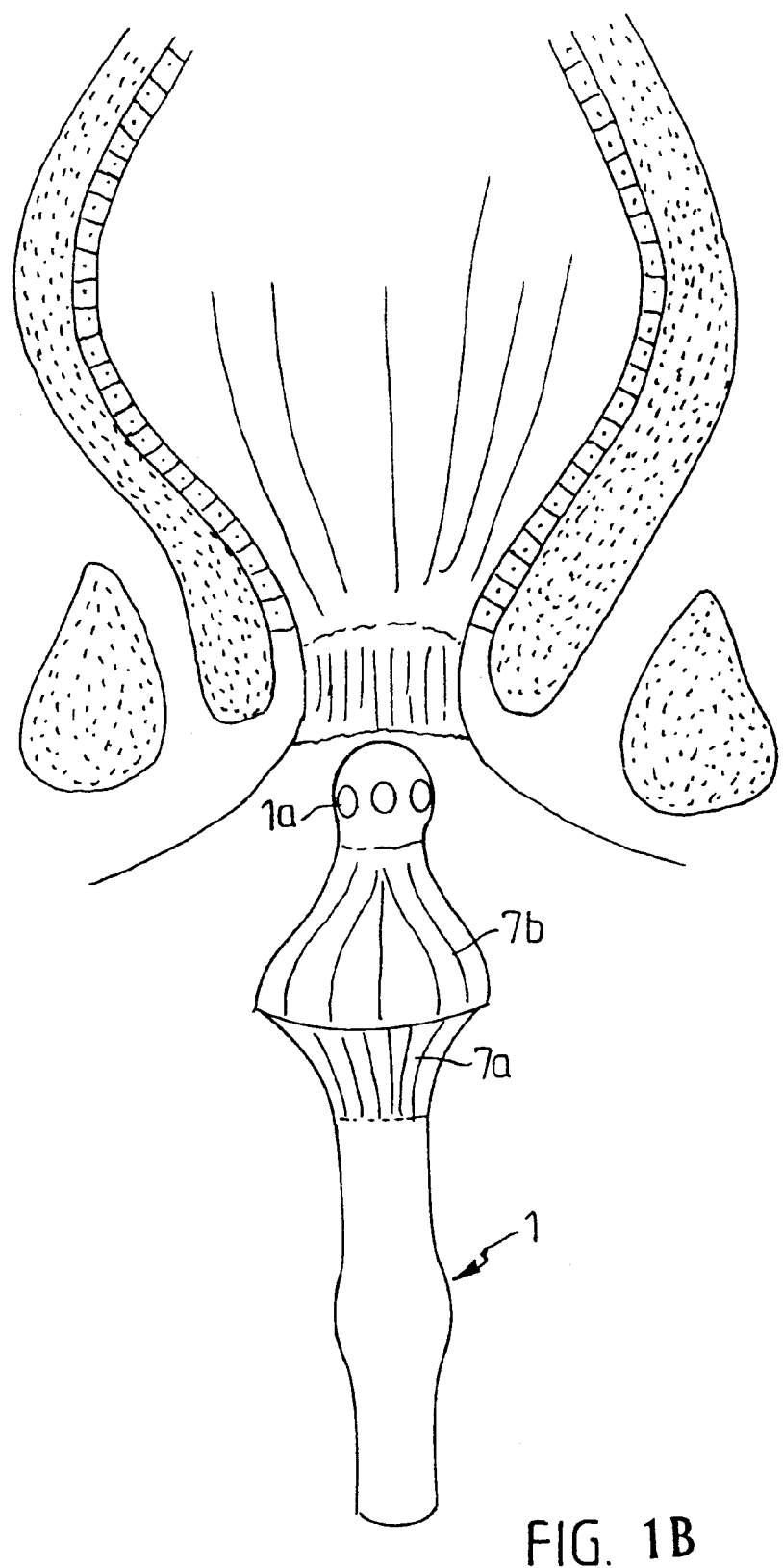
FIG. 1B is a partial view corresponding to that of FIG. 1A but with the expandable part of the apparatus in its non-expanded state before insertion into the rectum of a patient.
Figure 1C:
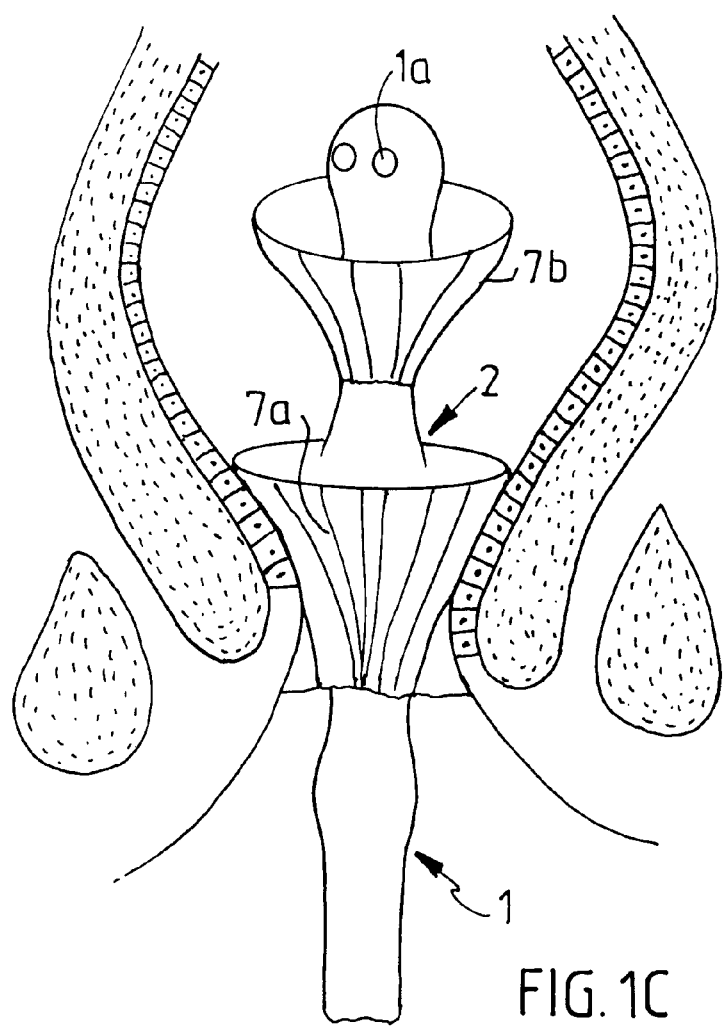
FIG. 1C is a partial view corresponding to that in FIG. 1B but showing the expandable part of the apparatus during insertion into the rectum.

The apparatus illustrated in FIGS. 1A to 1C comprises a holder part including a tubular member 1, and at one end of the tubular member 1, an expandable part 2. The latter is typically a balloon or a balloon-like member, for example made of silicone, and extends over an opening 3 (see FIG. 1A) of a channel (not shown) extending through the tubular member 1 and through which air (or other gas or fluid, if desired) may be supplied via a tube 4 attached to a branched tube part 5 of the tubular member 1 to inflate, or expand, the balloon. A through-channel (not shown) extends from the lower end of tubular member 1 to openings 1a (FIG. 1B) at the top end thereof and for permitting pressure equalization between the surroundings and the internal parts of the intestine when the apparatus is used. In the illustrated case, the through-channel is connected to a tube 6 attached to the tubular member 1.

The balloon 2 comprises a protective cover of flexible or resilient material. In the illustrated case, and as is best shown in FIG. 1B, the cover is of a two-part capsule or shell type, e.g. of plastics, such as PVC or silicone, comprising a rear (or lower) shell part 7a and a fore (or upper) shell part 7b. In the deflated state of the balloon shown in FIG. 1B, the fore shell part 7b slightly overlaps the rear shell part 7a such that the two shell parts together totally cover the balloon 2. (The terms "fore" and "rear", respectively, refer to the direction of inserting the instrument into the intestine). The rear shell part 7a is attached to tubular member 1 at the rear end of the shell part, and fore shell part 7b is attached to tubular member 1 at the fore end of the shell part, leaving the remainder of the two shell parts free from the balloon 2. Alternatively, the shell parts 7a, 7b are integral with the balloon 2.

Figure 2:
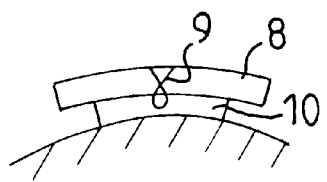
FIG. 2 is a schematic illustration of separate sampling material member on the expandable part of the apparatus shown in FIG. 1A.

The surface of the balloon 2 (FIG. 1A) has, on a central part thereof, a number of pads or patches 8 of absorptive material, e.g. cellulose, attached to the surface thereof, e.g. three or more patches equidistantly spaced along the balloon periphery. The patches 7 may be attached directly to the balloon 2, or, via another member attached to the balloon surface such as shown by way of example only in FIG. 2. Here, the patch 8 is attached, e.g. by a stitch 9, to a support member 10, e.g. also of cellulose, which in turn is attached to the surface of balloon 2, e.g. by gluing. In this way, the absorptive capability or structure of the patch is essentially unaffected by the attachment to the balloon.

Inflation and deflation, respectively, of the balloon 2 may be achieved by means of, for example, a syringe or a pumping device, such as a flexible or elastic ball or the like (not shown), connected to tube 4 (FIG. 1A). When inflating the balloon 2 from the deflated state shown in FIG. 1B, the fore and rear shell parts 7a, 7b are brought apart to expose the area of the balloon 2 supporting the patches 8 as shown in FIG. 1A. If the material of the shell parts is elastic, the two shell parts may in fact invert as illustrated in FIG. 1A, to expose a major part of the balloon surface. In use, the apparatus described above may readily be inserted through the anus of a patient to be tested. When in the non-inflated state, the diameter of the balloon is preferably smaller than the diameter of the anus i.e. smaller than about 15–20 mm (but larger than about 5 mm). For rectal sampling, for example, the apparatus is inserted to an appropriate position into the rectum of a patient, with the balloon 2 in the non-inflated state. Preferably, the patches 8 are moistened with water prior to using the apparatus. In FIG. 1A, the fore part of the apparatus with the balloon 2 has been inserted into the rectum beyond the internal sphincter, and the balloon has then been inflated to uncover the patches 8 and make them contact the colonic mucosa such as at 11. When such contact between the patches and mucosa has been maintained for a predetermined time, e.g. 10 to 15 minutes, the balloon is deflated. The deflation itself may cause the protective shell parts 7a, 7b to return to the patch protecting state shown in FIG. 1B where they enclose the patches 8. In the illustrated embodiment, however, the rear shell part 7a is returned to its protecting state by the forces acting upon the shell part when the balloon is retracted and forced through the anus. In both cases, the patches 8 with absorbed mucous fluid will be efficiently protected by the shell part 7a from further contact with the colonic wall and, importantly, when passing the internal sphincter. After the apparatus has been removed from the patient, the absorbing patches 8 which have been in contact with the colonic mucosa are removed from the balloon 2 and the absorbed contents is analysed, e.g. by extraction of the absorbing patches 8. The extract may then be analyzed by various methods for different substances, primarily proteins, enzymes or hormones. The patches may also be analyzed without extraction by adding directly to the patches, reagents which give a detectable reaction, e.g. a colour reaction, if the substance tested for is present in the pad and may also be a measure of the amount of the substance in question.

If the apparatus is used for allergy tests (such as food allergy, including celiac disease), provocation of the intestine may be effected by a desired food allergen (e.g. gluten) contained in the patches 8. In such a case, the period of contact between the intestinal mucosa and the patches 8 will, of course, be longer, say 15–60 minutes.

Figure 3A:
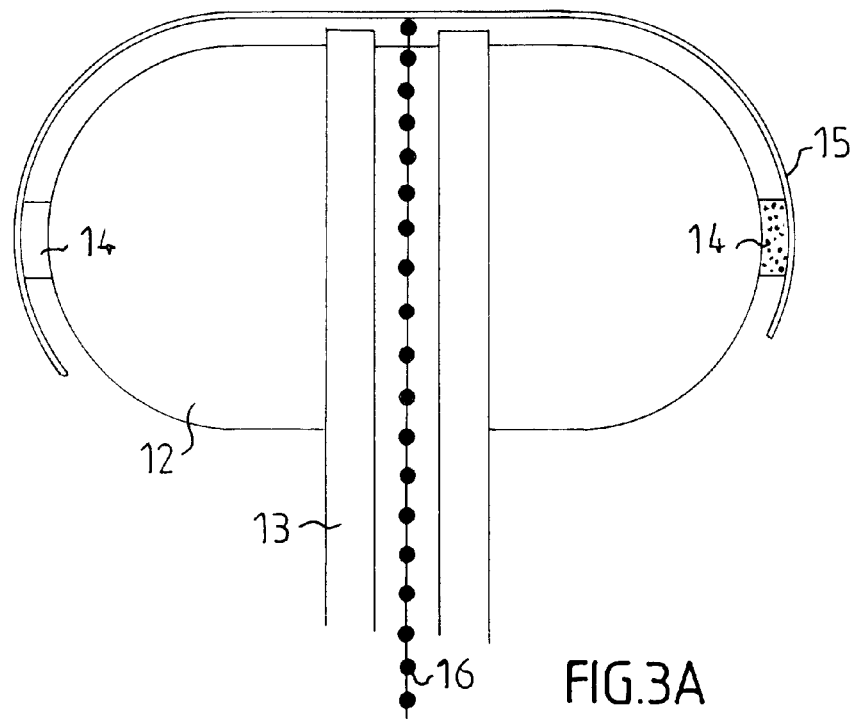
FIG. 3A is a schematic partial view in section of another embodiment of apparatus of the invention with the expandable apparatus part protected by protective means.
Figure 3B:
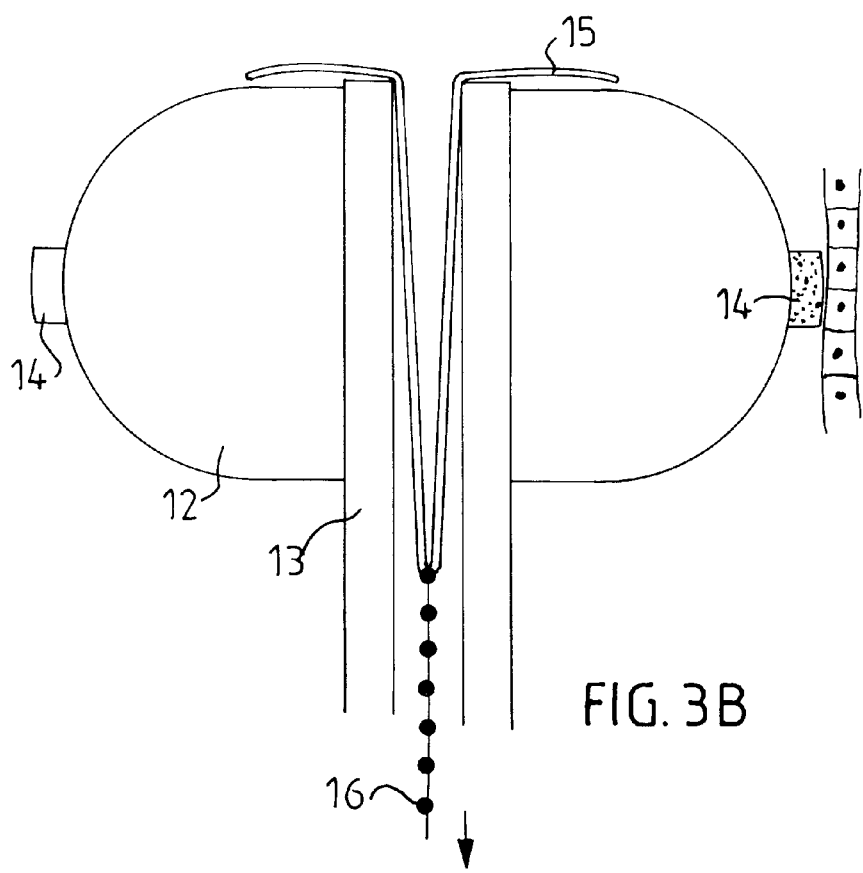
FIG. 3B is a corresponding view to that in FIG. 3A with the protection means of the expandable part withdrawn.

An alternative design of the expandable part of the apparatus of the present invention is shown in FIGS. 3A and 3B. Like the embodiment in FIGS. 1A to 1C, the expandable part comprises a balloon 12 attached to a tubular support 13 which may be a colonoscope or rectoscope, for example, or a device or instrument specially designed for the present purposes. For clarity, the balloon 12 is shown inflated in FIGS. 3A and 3B. A plurality of absorbing elements, such as pads or patches 14 of an absorbing material, are fixed to the balloon surface. A protective cover 15 of flexible material is attached to a pulling means 16, e.g. a rod or, as illustrated, a string extending within the tubular support 13. When pulling the string 16, the protective cover 15 is drawn into the interior of the tubular support 13 to expose the absorbing patches 14 on the balloon surface (FIG. 3B).

In use for taking a rectal sample in a patient to be tested, similarly as described above for embodiment in FIGS. 1A to 1C, the fore part of the illustrated apparatus, with the balloon in a deflated state, is inserted into the rectum of the patient to be tested, the cover 15 then efficiently protecting the absorbing patches 14 from contacting the patient's sphincter and the rectal wall. Once inserted to the desired position in the rectum, the balloon 12 is inflated. The cover 15 is then drawn into the tubular support 13 as shown in FIG. 3B, thereby exposing the absorbing patches 14 to make them contact the rectal wall and start absorbing material from the mucous surface thereof. After the predetermined contact time, the balloon 12 is deflated and the apparatus is removed from the patient. The patches 14 are then separated from the balloon and analysed as outlined above.

Figure 4:
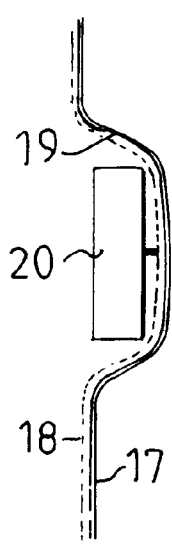
FIG. 4 is a schematic partial view in section of yet another embodiment of apparatus of the invention in a non-expanded state and showing a sampling surface element protected by being received in a recess in the expandable part.

FIG. 4 illustrates schematically yet an alternative design of the expandable part of the apparatus, where a tubular support 17 for a balloon 18 has a respective recess 19 for each absorbing patch 20. In the deflated state of the balloon 18, the patch 20 is received in the recess 19 with its top surface below the remaining balloon surface as shown in the figure, and thereby protected from contact with the intestinal wall. When the balloon is inflated, it will expand similarly as shown in, for example, FIG. 1A, to contact the patch with the intestinal wall. Upon deflation of the balloon, the patch 20 is sucked into the recess 19 by the negative pressure created in the deflation and is protected when removing the apparatus from the patient. Such recesses for the absorbing patches may, of course, also be used in combination with other apparatus variants of the invention like e.g. those illustrated in FIGS. 1A to 1C and FIGS. 3A and 3B, respectively.

Analysis of the absorbing material may be performed in various ways. A simple procedure is described below by way of example only. After the absorbing patches (8, 14) have been removed from the balloon (2, 12), they are immersed in an extraction buffer, e.g. cetyl-N,N,N-trimethylammonium bromide, 0.3% (w/v) in 0.9% saline. The extraction buffer may, for example, be contained in a syringe with the piston removed, e.g. 2 ml of extraction buffer in a 5 ml volume syringe. After a predetermined time, say, 1 hour, the buffer, including absorbed material contained in the patch or patches, is removed. In the case of a syringe being used, this is accomplished by re-inserting the piston into the syringe and pressing the liquid (including squeezing the patch or patches) into a suitable test container where the expelled liquid is analysed for the presence and, optionally, also quantity, of a desired analyte or desired analytes. Depending on the disease or disorder to be tested for, the analyte may, for example, be an inflammatory mediator, reflecting neutrophilic activity (e.g. myeloperoxidase), eosinophilic activity (ECP=eosinophil cationic protein), or EPO (eosinophil peroxidase or EPX), mast cell/basophilic activity (histamine or tryptase). Further possible analytes are certain cytokines (e.g. IL-6, IL-1, TNF-alfa), prostaglandins (e.g. PGE2).

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

What is claimed is:

1. An apparatus for taking an intestinal sample of a human or animal patient, said apparatus comprising a holder part and an expandable part supported by the holder part, the expandable part having one or more sampling areas on the surface thereof, said expandable part in a non-expanded state thereof being adapted for rectal insertion into and retraction from a patient's intestine, and in an expanded state, when inserted into a patient's intestine, being capable of contacting an intestinal wall with at least one sampling area, the apparatus further comprising protective means for preventing said sampling area or areas from contact with an intestinal wall and intestinal fluid at least when said expandable part in the non-expanded state thereof is being rectally inserted into a patient's intestine.

2. The apparatus according to claim 1, wherein the protective means prevent said sampling area or areas from contact with an intestinal wall and intestinal fluid also during retraction of said expandable part from a patient's intestine.

3. The apparatus according to claim 1, wherein the protective means comprise an at least partially movable protective cover capable of exposing said sampling area or areas in the expanded state of said expandable part.

4. The apparatus according to claim 3, wherein the protective cover comprises two cover parts extending lengthwise from opposed end portions of said expandable part and adapted to together cover said sampling area or areas at least in the non-expanded state of the expandable part.

5. The apparatus according to claim 4, wherein the two cover parts partially overlap each other at least in the non-expanded state of the expandable part.

6. The apparatus according to claim 3, wherein the protective cover is adapted to withdraw from and expose the sampling area or areas when the expandable part is being expanded.

7. The apparatus according to claim 3, wherein the protective cover after having been withdrawn from the sampling area or areas upon expansion of the expandable part, is capable of covering the sampling area when the expandable part is being contracted.

8. The apparatus according to claim 4, wherein the protective cover is a two-part cover comprising a fore cover part and a rear cover part and the rear cover part, after having been withdrawn from the sampling area or areas upon expansion of the expandable part, is capable of covering the sampling area or areas when the expandable part is being retracted from the intestine.

9. The apparatus according to claim 3, wherein the protective cover is capable of uncovering the sampling area or areas in the expanded state of the expandable part through operation of a mechanical actuator.

10. The apparatus according to claim 9, wherein the actuator comprises a pulling means.

11. The apparatus according to claim 9, wherein the holder part comprises a hollow section into which the cover is capable of being drawn by said actuator to thereby uncover said surface area or areas.

12. The apparatus according to claim 1, wherein the expandable part is movably mounted in said holder part, and adapted such that in the non-expanded state, at least a sampling area supporting portion of the expandable part is retracted into the holder part, and in the expanded state, the expandable part projects out of the holder part to expose the sampling area or areas.

13. The apparatus according to claim 12, wherein the expandable part is mounted in the holder part via telescopic displacement means.

14. The apparatus according to claim 1, wherein the protective means comprise a respective recess in the holder part adapted to receive each sampling area when the expandable part is in its non-expanded state.

15. The apparatus according to claim 1, wherein the expandable part comprises an inflatable flexible or elastic member.

16. The apparatus according to claim 15, wherein the expandable part comprises a balloon or elastic tube.

17. The apparatus according to claim 1, wherein each sampling area comprises a surface element attached to the expandable part.

18. The apparatus according to claim 17, wherein the surface element or elements are capable of absorbing fluid from an intestinal wall when contacted therewith.

19. The apparatus according to claim 1, wherein at least one sampling area comprises an immobilized receptor for an analyte in intestinal fluid.

20. The apparatus according to claim 1, wherein at least one sampling area contains a diffusible allergen.

21. The apparatus according to claim 1, wherein the expandable part comprises at least one surface area containing diffusible allergen, which surface area is different from the sampling area or areas.

22. The apparatus according to claim 1, wherein the holder part comprises a duct for pressure equilibration between the intestine and an external air pressure when the apparatus is inserted into a patient.

23. The apparatus according to claim 9, wherein the mechanical actuator comprises a string or rod.

24. An apparatus for taking an intestinal sample of a human or animal patient, said apparatus comprising a holder part and an expandable part supported by the holder part, the expandable part having one or more sampling areas on the surface thereof, said expandable part in a non-expanded state thereof being adapted for rectal insertion into and retraction from a patient's intestine, and in an expanded state, when inserted into a patient's intestine, being capable of contacting an intestinal wall with at least one sampling area, the apparatus further comprising a protective cover adapted to prevent said sampling area or areas from contact with an intestinal wall and intestinal fluid at least when said expandable part in the non-expanded state thereof is being rectally inserted into a patient's intestine.

25. A method for testing for allergy, comprising taking an intestinal sample of a human or animal patient using an apparatus comprising a holder part and an expandable part supported by the holder part, the expandable part having one or more sampling areas on the surface thereof, said expandable part in a non-expanded state thereof being adapted for rectal insertion into and retraction from a patient's intestine, and in an expanded state, when inserted into a patient's intestine, being capable of contacting an intestinal wall with at least one sampling area, the apparatus further comprising protective means for preventing said sampling area or areas from contact with an intestinal wall and intestinal fluid at least when said expandable part in the non-expanded state thereof is being rectally inserted into a patient's intestine, and analyzing the intestinal sample.

26. The method of claim 25, wherein the allergy is a food allergy.

27. The method according to claim 26, wherein the food allergy is celiac disease.

* * * * *